United States Patent [19]

Ryan

[11] 4,131,614

[45] Dec. 26, 1978

[54] PROCESS FOR PREPARING CIS-HEXAHYDRODIBENZOPYRANONES

[75] Inventor: Charles W. Ryan, Indianapolis, Ind.

[73] Assignee: Eli Lilly and Company, Indianapolis, Ind.

[21] Appl. No.: 831,458

[22] Filed: Sep. 8, 1977

Related U.S. Application Data

[63] Continuation-in-part of Ser. No. 702,806, Jul. 6, 1976, abandoned.

[51] Int. Cl.$^2$ .......................................... C07D 311/78
[52] U.S. Cl. .................................................. 260/345.3
[58] Field of Search ....................................... 260/345.3

[56] References Cited
PUBLICATIONS

Archer et al, J. Org. Chem., 42, 2277 (1977).
Razdan et al, JACS, 96, 5860 (1974).
Razdan et al, Tetrahedron Letters, pp. 4947-4950 (1969).

Primary Examiner—Nicky Chan
Attorney, Agent, or Firm—Charles W. Ashbrook; Arthur R. Whale

[57] ABSTRACT

Reaction of a 5-substituted resorcinol with a 1-alkoxy-4-(1-hydroxy-1-methylethyl)-1,4-cyclohexadiene in the presence of a catalyst such as boron tribromide, boron trifluoride or stannic chloride, and in the presence of about an equimolar quantity of water, affords predominantly a cis-hexahydrodibenzopyranone in high yields.

9 Claims, No Drawings

PROCESS FOR PREPARING CIS-HEXAHYDRODIBENZOPYRANONES

CROSS REFERENCE TO RELATED APPLICATIONS

This is a continuation-in-part of application Ser. No. 702,806 filed July 6, 1976, now abandoned.

BACKGROUND OF THE INVENTION

Certain hexahydrodibenzopyranones have recently been found to be useful in the treatment of anxiety, depression, and analgesia; see U.S. Pat. Nos. 3,928,598, 3,944,673 and 3,953,603. Of particular importance among such compounds are the 1-hydroxy-3-substituted-6,6-dimethyl-6,6a,7,8,10,10a-hexahydro-9H-dibenzo[b,d]pyran-9-ones, especially the 6a,10a-trans isomers which are somewhat more active pharmacologically than the corresponding 6a,10a-cis isomers. The prior art preparation of such 6a,10a-trans-hexahydrodibenzopyranones suffers from being multistep and of low overall yields; see Fahrenholtz, Lurie and Kierstead, J. Am. Chem. Soc. 88, 2079 (1966), 89, 5934 (1967). A new synthesis of 6a,10a-trans-hexahydrodibenzopyranones has recently been discovered which involves reaction of the corresponding 6a,10a-cis isomer with an aluminum halide to effect complete epimerization to provide exclusively the 6a,10a-trans isomer. Such epimerization process is the subject of Blanchard and Ryan's co-pending application Ser. No. 702,807 filed July 6, 1976, now U.S. Pat. No. 4,054,582. It has also been recently discovered that cis-1-hydroxy-3-substituted-6,6-dimethyl-6,6a,7,8,10,10a-hexahydro-9H-dibenzo[b,d]pyran-9-ones are readily prepared in one step by reaction of a 1-alkoxy-4-(1-hydroxy-1-methylethyl)-1,4-cyclohexadiene with a 5-substituted resorcinol in the presence of a catalyst such as boron tribromide, boron trifluoride or stannic chloride. Such condensation reaction is the subject of Day and Lavagnino's co-pending application filed this even date herewith.

An object of this invention is to provide an improvement in the above-referenced process for preparing dl-cis-1-hydroxy-3-substituted-6,6-dimethyl-6,6a,7,8,10,10a-hexahydro-9H-dibenzo[b,d]pyran-9-ones from 5-substituted resorcinols and 1-alkoxy-4-(1-hydroxy-1-methylethyl)-1,4-cyclohexadienes.

SUMMARY OF THE INVENTION

In fulfillment of the above and other objects, this invention provides, in a process for preparing a dl-cis-hexahydrodibenzopyranone of the general formula

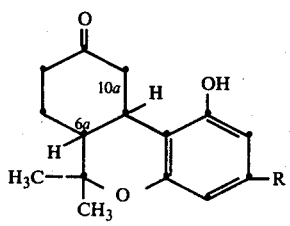

wherein R is $C_5$–$C_{10}$ alkyl, $C_5$–$C_{10}$ alkenyl, $C_5$–$C_8$ cycloalkyl, or $C_5$–$C_8$ cycloalkenyl, and wherein the hydrogen atoms attached at the 6a and 10a positions are oriented cis to one another, which includes reacting a 5-substituted resorcinol of the formula

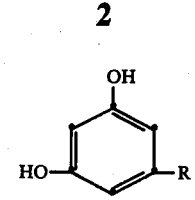

wherein R has the above-defined meaning, with a 1-alkoxy-4-(1-hydroxy-1-methylethyl)-1,4-cyclohexadiene having the formula

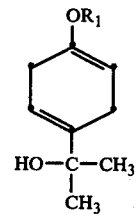

wherein $R_1$ is $C_1$–$C_4$ alkyl, in the presence of a catalyst selected from boron tribromide, boron trifluoride, and stannic chloride, in an organic solvent at a temperature from about $-30°$ C. to about $100°$ C., the improvement comprising adding about an equimolar quantity of water to the reaction mixture. The addition of water to the reaction of a resorcinol and the aforementioned cyclohexadiene derivative in accordance with the process of this invention effects about a 20 to about a 25 percent increase in the yield of the cis-hexahydrodibenzopyranone product produced thereby.

DETAILED DESCRIPTION OF THE INVENTION

In accordance with the process of this invention, a 1-alkoxy-4-(1-hydroxy-1-methylethyl)-1,4-cyclohexadiene is condensed with approximately an equimolar quantity of a 5-substituted resorcinol in the presence of a catalyst selected from boron tribromide, boron trifluoride, and stannic chloride, in an organic solvent, and in the presence of about an equimolar quantity of water. In the above formulas, R is defined as $C_5$–$C_{10}$ alkenyl, $C_5$–$C_8$ cycloalkyl, and $C_5$–$C_8$ cycloalkenyl. Examples of $C_5$–$C_{10}$ alkyl groups include n-pentyl, 1,1-dimethylpentyl, n-hexyl, 1-ethylhexyl, 1,2-dimethylheptyl, 1-ethyl-2-methylhexyl, 1,2,3-trimethylheptyl, n-octyl, 1-methylnonyl, and n-decyl. Similarly, typical $C_5$–$C_{10}$ alkenyl groups include 3-methyl-2-butenyl, 1-pentenyl, 1,2-dimethyl-1-hexenyl, 2-heptenyl, 1-ethyl-2-heptenyl, 1,1-dimethyl-2-octenyl, 3-nonenyl, 1,2-dimethyl-1-heptenyl, and 1-methyl-1-nonenyl. R additionally includes $C_5$–$C_8$ cycloalkyl groups such as cyclohexyl, cycloheptyl and cyclooctyl, as well as $C_5$–$C_8$ cycloalkenyl groups such as 1-cyclopentenyl, 1-cyclohexenyl, 2-cycloheptenyl, and 3-cyclooctenyl. Typical 5-substituted resorcinols commonly utilized in the process of this invention thus include 5-(n-pentyl)resorcinol, 5-(1,2-dimethylheptyl)resorcinol, 5-(1-ethyl-2-methylbutyl)-resorcinol, 5-(n-octyl)resorcinol, 5-(1-hexenyl)-resorcinol, 5-(1,2-dimethyl-1-heptenyl)resorcinol, 5-(1-octenyl)resorcinol, 5-cyclopentylresorcinol, 5-cycloheptylresorcinol, 5-(1-cyclohexenyl)resorcinol, 5-(2-cyclooctenyl)resorcinol, and the like.

$R_1$ in the above formula representing the cyclohexadiene derivative defines a $C_1$–$C_4$ alkyl group such as methyl, ethyl, n-butyl and isobutyl. Preferred cyclohexadiene derivatives have the above formula wherein $R_1$ is methyl or ethyl.

This invention provides a convenient process for preparing a dl-cis-hexahydro-dibenzo[b,d]pyran-9-one. As used herein, the term "cis" refers to the orientation relative to one another of the hydrogen atoms attached at the 6a and 10a positions of a dibenzopyranone compound represented by the above formula. Accordingly, compounds which are designated as being "cis" are those dibenzopyranones of the above formula wherein the hydrogen atoms attached at the 6a and the 10a positions are oriented on the same side of the plane of the molecule. It will be recognized that at least two isomers are included by the "cis" designation. In particular, both the 6a hydrogen atom and the 10a hydrogen atom can be oriented above the plane of the molecule, in which case their absolute configuration is designated as 6aβ and 10aβ. Alternatively, both the 6a hydrogen atom and the 10a hydrogen atom can be oriented below the plane of the molecule, in which case they are designated as 6aα and 10aα.

The absolute configuration of the 6a-hydrogen atom and the 10a-hydrogen atom will not hereinafter be designated; rather, it is to be understood that the designation "cis" includes the separate mirror image isomers of the compounds having the above general formula, as well as the dl mixture of such mirror image isomers. For example, a 6a,10a-cis compound prepared by the process of this invention will be understood to include the 6aα,10aα-isomer, as well as the 6aβ,10aβ isomer, or a mixture of said mirror images. Such mixture of mirror image isomers will be designated in the normal manner as a dl-mixture, and is the usual product of the present process.

The process provided by this invention is carried out by mixing approximately equimolar quantities of a 5-substituted resorcinol, as hereinabove defined, a 1-alkoxy-4-(1-hydroxy-1-methylethyl)-1,4-cyclohexadiene, and water, in an unreactive organic solvent and in the presence of a catalyst selected from boron tribromide, boron trifluoride and stannic chloride. Unreactive organic solvents commonly used in the process include halogenated hydrocarbons such as dichloromethane, chloroform, 1,2-dibromoethane, 1-bromo-2-chloroethane, 1,1-dibromoethane, 2-chloropropane, 1-iodopropane, chlorobenzene, bromobenzene, and 1,2-dichlorobenzene; aromatic solvents such as benzene, toluene, and xylene; and ethers such as diethyl ether, methyl ether ether, dimethyl ether, and diisopropyl ether. Preferred unreactive organic solvents include the halogenated hydrocarbons and the aromatic solvents. A preferred catalyst for the reaction is stannic chloride. When boron trifluoride is utilized as condensation catalyst, it generally is utilized as the commercially available diethyl ethereate complex. The quantity of catalyst generally incorporated in the process ranges from about an equimolar quantity, relative to the resorcinol and cyclohexadiene reactants, to an excess of about 0.1 to about a 5 molar excess. The process of this invention can be carried out at a temperature in the range of from about −30° C. to about 100° C., and is most conveniently carried out at a temperature in the range of from about −10° C. to about 40° C., especially from about 0° C. to about 25° C. As an example, a resorcinol such as 5-(n-pentyl)resorcinol is mixed with about an equimolar quantity of 1-methoxy-4-(1-hydroxy-1-methylethyl)-1,4-cyclohexadiene in a solvent such as benzene. Approximately an equimolar quantity of water is added to the reaction mixture, and a catalyst such as boron trifluoride diethyl ethereate is added in the amount of about a 0.1 to about a 5 molar excess. The reaction is conducted at a temperature in the range of about −20° C. to about 100° C., and is substantially complete within about 0.5 to about 8 hours; however, longer reaction times are not detrimental to the process and can be utilized if desired.

Upon completion of the reaction of a 5-substituted resorcinol and the aforementioned cyclohexadiene derivative according to the above-recited process conditions, the product, a dl-cis-1-hydroxy-3-substituted-6,6-dimethyl-6,6a,7,8,10,10a-hexahydro-9H-dibenzo[b,d]pyran-9-one, is isolated by simply washing the reaction mixture with an aqueous acid or an aqueous base, or both successively, followed by washing the reaction mixture with water. The organic solvent layer is then separated and the solvent is removed therefrom, for example by evaporation. Aqueous acids commonly used to wash the reaction mixture include dilute aqueous hydrochloric acid and dilute aqueous sulfuric acid, for instance 0.5 to about 6 normal aqueous acids. Commonly used aqueous bases include 0.1 to 1.0 N sodium hydroxide, as well as saturated sodium bicarbonate solutions. Once the product of the reaction is isolated by removal of the reaction solvent, no further purification generally is required, although the product can be recrystallized from solvents such as n-hexane and cyclohexane if desired. The product produced according to the process of this invention is substantially exclusively the dl-cis-isomer of a 1-hydroxy-3-substituted-6,6-dimethyl-6,6a,7,8,10,10a-hexahydro-9H-dibenzo[b,d]pyran-9-one, although small quantities on the order of about 5 to about 15 percent by weight of the corresponding dl-trans isomer generally can be detected. Purification of such mixture to remove the trans isomers which are present is unnecessary since the major product, namely the dl-cis-hexahydrodibenzopyranone, is generally transformed to the pure dl-trans isomer by treatment with an aluminum halide, as is described in more detail hereinbelow.

As hereinabove noted, this invention provides the improvement of the addition of approximately an equimolar quantity of water to the condensation reaction of a 5-substituted resorcinol with a 1-alkoxy-4-(1-hydroxy-1-methylethyl)-1,4-cyclohexadiene in the presence of a catalyst in an unreactive organic solvent. While an equimolar quantity of water relative to the resorcinol and to the cyclohexadiene derivative generally is utilized in the process of this invention, larger quantities, such as from about a 0.1 to about a 1.0 molar excess for instance, can be incorporated if desired. The incorporation of water into the condensation of a resorcinol and the aforementioned cyclohexadiene derivative according to the process of this invention effects an increase in the yield of the dl-cis-hexahydrodibenzopyranone derivative which is produced. Such increase in yield typically ranges from about a 20 to about a 25 percent increase. In particular, when a 5-substituted resorcinol is condensed with a 1-alkoxy-4-(1-hydroxy-1-methylethyl)-1,4-cyclohexadiene in the presence of a catalyst such as stannic chloride in an organic solvent such as dichloromethane according to the process of Day and Lavagnino, which process is the subject of their co-pending application filed this even date herewith, the yield of the dl-cis-1-hydroxy-3-substituted-6,6-dimethyl-6,6a,7,8,10,10a-hexahydro-9H-dibenzo[b,d]pyran-9-one typically is about 55 to about 60 percent. When the same condensation of a resorcinol and the aforementioned cyclohexadiene derivative is carried out in accordance with the process of this invention, namely when about an equimolar quantity of water is added to the reaction mixture, the yield of the dl-cis-hexahydrodibenzopyranone which is produced suprisingly is about 75 to about 85 percent. The improved process provided by this invention thus affords significantly increased yields of cis-hexahydrodibenzopyranones prepared from 5-substituted resorcinols and 1-alkoxy-4-(1-hydroxy-1-methylethyl)-1,4-cyclohexaidenes.

The compounds which are prepared according to the process of this invention are substantially exclusively dl-cis-1-hydroxy-3-substituted-6,6-dimethyl-6,6a,7,8,10,10a-hexahydro-9H-dibenzo[b,d]pyran-9-ones. such cis-hexanhydrodibenzopyranones, while pharmacologically active themselves, are somewhat less active pharmacologically than the corresponding trans isomer. Such dl-cis-hexahydrodibenzopyranones are useful, however, as intermediates in the preparation of the more pharmacologically active dl-trans-hexahydrodibenzopyranones. In particular, reaction of a dl-cis-hexahydrodibenzopyranone, which is prepared according to the process of this invention, with an aluminum halide such as aluminum bromide or aluminum chloride in a halogenated hydrocarbon solvent such as dichloromethane effects total epimerization to afford exclusively the corresponding dl-trans-hexahydrodibenzopyranone. As an example, dl-cis-1-hydroxy-3-(1,1-dimethylheptyl)-6,6-dimethyl-6,6a,7,8,10,10a-hexahydro-9H-dibenzo[b,d]pyran-9-one, which is prepared in about 80 to about 85 percent yield in accordance with the process of this invention, can be reacted with about a 3 to 4 molar excess of aluminum chloride in dichloromethane at a temperature of about 25° C. to provide exclusively dl-trans-1-hydroxy-3-(1,1-dimethylheptyl)-6,6-dimethyl-6,6a,7,8,10,10a-hexahydro-9H-dibenzo[b,d]pyran-9-one. As noted hereinbefore, such trans-hexahydrodibenzopyranones are particularly useful in the treatment of anxiety and depression.

In an effort to more fully describe the process provided by this invention, the following detailed examples are presented by way of illustration.

EXAMPLE 1 dl-cis-1-Hydroxy-3-(1,1-dimethylheptyl)-6,6-dimethyl-6,6a,7,8,10,10a-hexahydro-9H-dibenzo[b,d]pyran-9-one A solution of 11.8 g. of 5-(1,1-dimethylheptyl)-resorcinol and 10.0 g. of 1-methoxy-4-(1-hydroxy-1-methylethyl)-1,4-cyclohexadiene in 200 ml. of commercial grade dichloromethane was stirred and cooled to about −10° C. in an ice/acetone bath. To the cold stirred reaction mixture was added, in one portion, 0.9 ml. of water, and, dropwise over fifteen minutes, 13 ml. of stannic chloride. During the addition of the stannic chloride to the reaction mixture, the temperature of the mixture increased from −10° C. to +5° C. and it was stirred for seven hours. The reaction mixture then was washed with water, with 2N hydrochloric acid, with 1N sodium hydroxide, and again with water. After drying the washed reaction mixture, the solvent was removed therefrom by evaporation under reduced pressure to provide the product as a solid. The solid so formed was recrystallized from 100 ml. of hot n-hexane, affording 15.5 g. (83 percent yield) of dl-cis-1-hydroxy-3-(1,1-dimethylheptyl)-6,6-dimethyl-6,6a,7,8,10,10a-hexahydro-9H-dibenzo[b,d]pyran-9-one. M.P. 153–158° C. Gas-liquid chromatography indicated that the product contained about 13 percent of the dl-transisomer.

EXAMPLE 2 dl-cis-1-Hydroxy-3-(1,1-dimethlheptyl)-6,6-dimethyl-6,6a,7,8,10,10a-hexahydro-9H-dibenzo[b,d]-pyran-9-one A solution of 11.8 g. of 5-(1,1-dimethylheptyl)-resorcinol and 10.0 g. of 1-methoxy-4-(1-hydroxy-1-methylethyl)-1,4-cyclohexadiene in 200 ml. of commercial grade dichloromethane was stirred and cooled to about −10° C. in an ice/acetone bath. To the cold stirred reaction mixture was added, dropwise over fifteen minutes, 13 ml. of stannic chloride. The temperature of the reaction mixture increased from −10° C. to 5° C. during the addition of the stannic chloride. Following the complete addition of the stannic chloride to the reaction mixture, the mixture was stirred for seven hours at a temperature of about 0 to 5° C. The reaction mixture was then washed with water, with 2N hydrochloric acid, with 1N sodium hydroxide, and again with water. The reaction mixture was dried and the solvent was removed therefrom by evaporation under reduced pressure to provide the product as a solid. The product so formed was recrystallized from 100 ml. of hot n-hexane, affording 11.1 g. (60 percent yield) of dl-cis-1-hydroxy-3-(1,1-dimethylheptyl)-6,6-dimethyl-6,6a,7,8,10,10a-hexahydro-9H-dibenzo[b,d]pyran-9-one. M.P. 153–158° C. Gas-liquid chromatography indicated that the product contained about 13.2 percent of the dl-trans isomer.

EXAMPLE 3 dl-cis-1-Hydroxy-3-(1,1-dimethylheptyl)-6,6-dimethyl-6,6a,7,8,10,10a-hexahydro-9H-dibenzo[b,d]pyran-9-one.

The process of Example 1 was followed in general, except that the reaction mixture was cooled to −30° C. before the addition of the stannic chloride, which addition was dropwise over a period of 30 Minutes. After the addition, the mixture was stirred for seven hours at 0° C. The product was 16.8 g. of dl-cis-1hydroxy-3-(1,1-dimethylheptyl)-6,6-dimethyl-6,6a,7,8,10,10a-hexahydro-9H-dibenzo[b,d]pyran-9-one, which was found by thin layer chromatography to be identical to the product of Example 1.

EXAMPLE 4 dl-cis-1-Hydroxy-3-(1,1-dimethylheptyl)-6,6-dimethyl-6,6a,7,8,10,10a-hexahydro-9H-dibenzo[b,d]pyran-9-one.

The process of Example 1 was followed, except that the temperature before the addition of the stannic chloride was −20° C. The yield was 17.5 g. of dl-cis-1-hydroxy-3-(1,1-dimethylheptyl)-6,6-dimethyl-6,6a,7,8,10,10a-hexahydro-9H-dibenzo[b,d]pyran-9-one, which was determined by thin layer chromatography to be identical to the product of Example 1.

EXAMPLE 5 dl-cis-1Hydroxy-3-(1,1-dimethylheptyl)-6,6-dimethyl-6,6a,7,8,10,10a-hexahydro-9H-dibenzo[b,d]pyran-9-one.

The process of Example 1 was followed again except the temperature before the addition of the stannic chloride was −9° C., and the addition was dropwise over a period of one hour. The product was 16.4 g. of dl-cis-1-hydroxy-3-(1,1-dimethylheptyl)-6,6-dimethyl-6,6a,7,8,10,10a-hexahydro-9H-dibenzo[b,d]pyran-9-one,

EXAMPLE 6 d1-cis-1-Hydroxy-3-(1,1-dimethylheptyl)-6,6-dimethyl-6,6a,7,8,10,10a-hexahydro-9H-dibenzo[b,d] pyran-9-one.

The process of Example 1 was repeated, except that the initial temperature was 10° C. and the stannic chloride was added dropwise rapidly. After the addition, the reaction mixture was heated to the reflux temperature and held at that temperature while it was stirred for seven hours. The product was 13.7 g. of d1-cis-1-hydroxy-3-(1,1-dimethylheptyl)-6,6-dimethyl-6,6a,7,8,10,10a-hexahydro-9H-dibenzo[b,d]pyran-9-one, identical to the product of the examples above by thin layer chromatography.

EXAMPLE 7 d1-cis-1-Hydroxy-3-(1,1-dimethylheptyl)-6,6-dimethyl-6,6a,7,8,10,10a-hexahydro-9H-dibenzo[b,d]pyran-9-one.

The process of Example 6 was followed again, except that the initial temperature was 5° C. and the reaction mixture was allowed to warm to the ambient temperature while it was stirred for seven hours. The product was 15.1 g. of d1-cis-1-hydroxy-3-(1,1-dimethylheptyl)-6,6-dimethyl-6,6a,7,8,10,10a-hexahydro-9H-dibenzo[b,d]pyran-9-one, identical to the product of Example 1 by thin layer chromatography.

EXAMPLE 8 d1-cis-1-Hydroxy-3-(1,1-dimethylheptyl)-6,6-dimethyl-6,6a,7,8,10,10a-hexahydro-9H-dibenzo[b,d]pyran-9-one.

A solution of 4.72 g. of 5-(1,1-dimethylheptyl) resorcinol and 4.7 g. of 1-isopropoxy-4-(1-hydroxy-1-methylethyl)-1,4-cyclohexadiene in 150 ml. of commercial grade dichloromethane containing 0.3 ml. of water was stirred at −10° C. while 3.5 ml. of stannic chloride was added dropwise. The reaction mixture was stirred for seven hours at 0° C., and then was worked up according to the method described in Example 1. The product was d1-cis-1-hydroxy-3-(1,1-9H-dibenzo[b,d]-pyran-9-one, identified by thin layer chromatography as identical to the product of Example 1.

EXAMPLE 9 d1-cis-1-Hydroxy-3-(1,1-dimethylheptyl)-6,6-dimethyl-6,6a,7,8,10,10a-hexahydro-9H-dibenzo[b,d]pyran-9-one.

Following the procedure outlined in Example 1, 4.72 g. of 5-(1,1;L-dimethylheptyl)resorcinol was reacted with 4.32 g. of 1-ethoxy-4-(1-hydroxy-1-methylethyl)-1,4-cyclohexadiene in 100 ml. of cyclohexane-stabilized dichloromethane (i.e., commercial grade) containing a small amount of water. The reaction mixture was stirred at 0° C. while 6 ml. of stannic chloride was added dropwise. The reaction mixture then was stirred for six hours at 5° C., and then worked up in the normal fashion. The residue was slurried in 25 ml. of hot hexane, chilled and the collected precipitate was identified as 3.65 g. of d1-cis-1-hydroxy-3-(1,1-dimethylheptyl)-6,6-dimethyl-6,6a,7,8,10,10a-hexahydro-9H-dibenzo[b,d]pyran-9-one, shown by thin layer chromatography to be identical to the product of Example 1.

EXAMPLE 10 d1-trans-1-Hydroxy-3-n-pentyl-6,6-dimethyl-6,6a,7,8,10,10a-hexahydro-9H-dibenzo[b,d]pyran-9-one.

A solution of 400 mg. of d1-cis-1-hydroxy-3-n-pentyl-6,6-dimethyl-6,6a,7,8,10,10a-hexahydro-9H-dibenzo[b,d]pyran-9one in 200 ml. of commercial grade dichloromethane was stirred at 24° C. while 600 mg. of aluminum chloride was added in one portion. The reaction mixture then was stirred at 24° C. for two hours. After washing the reaction mixture with water and then drying the organic solution, the solvent was removed by evaporation under reduced pressure, leaving the product as a solid. The solid so formed was recrystallized from n-hexane to afford 220 mg. of d1-trans-1-hydroxy-3-n-ptentyl-6,6-dimethyl-6,6a,7,8,10,10a-hexahydro-9H-dibenzo[b,d]pyran-9one. M.P. 146–150° C.

EXAMPLE 11 d1-trans-1-Hydroxy-3-(1,1-dimethylheptyl)-6,6-dimethyl-6,6a,7,8,10,10a-hexahydro-9H-dibenzo[b,d]-pyran-9-one.

A solution of 1.0 g. of d1-cis-1-hydroxy-3-(1,1-dimethylheptyl)-6,6-dimethyl-6,6a,7,8,10,10a-hexahydro-9H-dibenzo[b,d]pyran-9-one in 40 ml. of commercial grade dichloromethane was stirred at 24° C. while 1.0 g. of aluminum chloride was added in one portion. The reaction mixture was stirred at 24° C. for five hours. The reaction mixture was then washed with 1N hydrochloric acid solution and with water. After drying the organic solution, the solvent was removed therefrom by evaporation under reduced pressure, providing 994 mg. of the product as a solid. The solid so formed was recrystallized from hexane to afford 761 mg. of d1-trans-1-hydroxy-3-(1,1-dimethylheptyl)-6,6-dimethyl-6,6a,7,8,10,10a-hexahydro-9H-dibenzo[b,d]-pyran-9-one. M.P. 160–161° C.

I claim:

1. In a process for preparing a cis-hexahydrodibenzopyranone of the formula

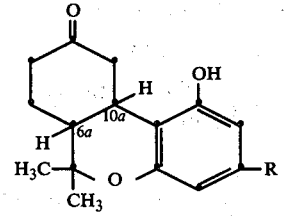

wherein:
R is $C_5$–$C_{10}$ alkyl, $C_5$–$C_{10}$ alkenyl, $C_5$–$C_8$ cycloalkyl or $C_5$–$C_8$ cycloalkenyl, and wherein the hydrogen atoms attached at the 6a and 10a positions are oriented cis to one another, which includes reacting a 5-substituted resorcinol of the formula

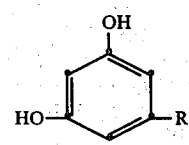

wherein R has the above-defined meaning, with a 1-alkoxy-4-(1-hydroxy-1-methylethyl)-1,4-cyclohexadiene of the formula

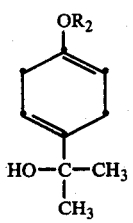

wherein $R_2$ is $C_1$–$C_4$ alkyl, in the presence of a catalyst selected from boron tribromide, boron trifluoride, and stannic chloride, in an unreactive organic solvent, the improvement comprising adding about an equimolar quantity of water to the reaction mixture.

2. The process according to claim 1 wherein the unreactive organic solvent is a halogenated hydrocarbon or an aromatic solvent.

3. The process according to claim 2 wherein the unreactive organic solvent is dichloromethane or benzene.

4. The process according to claim 2 wherein the catalyst is boron trifluoride diethyl ethereate.

5. The process according to claim 2 wherein the catalyst is stannic chloride.

6. The process according to claim 2, wherein in the resorcinol reactant, R is $C_5$–$C_{10}$ alkyl.

7. The process according to claim 6, wherein in the cyclohexadiene derivative utilized, $R_2$ is methyl or ethyl.

8. The process according to claim 7, said process comprising reacting 5-(1,1-dimethylheptyl)resorcinol with 1-methoxy-4-(1-hydroxy-1-methylethyl)-1,4-cyclohexadiene in the presence of stannic chloride in dichloromethane containing about an equimolar quantity of water relative to the resorcinol derivative.

9. The process according to claim 7, said process comprising reacting 5-(1,1-dimethylheptyl)resorcinol with 1-ethoxy-4-(1-hydroxy-1-methylethyl)-1,4-cyclohexadiene in the presence of stannic chloride in dichloromethane containing about an equimolar quantity of water relative to the resorcinol derivative.

* * * * *

UNITED STATES PATENT AND TRADEMARK OFFICE
CERTIFICATE OF CORRECTION

PATENT NO. : 4,131,614
DATED : December 26, 1978
INVENTOR(S) : Charles W. Ryan

It is certified that error appears in the above-identified patent and that said Letters Patent are hereby corrected as shown below:

Column 5, line 16, "9-ones. such cis-hexanhydrodibenzopyranones should read --9-ones. Such cis-hexahydrodibenzopyranones--

Column 5, line 58, after "+5°C.", insert --The temperature of the reaction mixture was maintained at 0 to 5°C.--

Column 6, line 2, "dl-transisomer" should read --dl-trans isomer--.

Column 6, line 41, "dl-cis-1hydroxy-" should read --dl-cis-1-hydroxy- --.

Column 7, line 45, "dl-cis-1-hydroxy-3-(1,1-9H dibenzo" should read --dl-cis-1-hydroxy-3-(1,1-dimethylheptyl)-6,6-dimethyl-6,6a,7,8,10,10a-hexahydro-9H-dibenzo--.

Column 7, line 55, "(1,1,L-dimethylheptyl) should read --(1,1-dimethylheptyl)--.

Column 8, line 16, "n-ptentyl" should read --n-pentyl--.

Signed and Sealed this

Seventeenth Day of July 1979

[SEAL]

Attest:

LUTRELLE F. PARKER
*Attesting Officer*   *Acting Commissioner of Patents and Trademarks*